United States Patent [19]
Komives et al.

[11] Patent Number: 5,143,066
[45] Date of Patent: Sep. 1, 1992

[54] OPTICAL FIBER SENSORS FOR CONTINUOUS MONITORING OF BIOCHEMICALS AND RELATED METHOD

[75] Inventors: Claire Komives; Jerome S. Schultz, both of Pittsburgh, Pa.

[73] Assignee: University of Pittsburgh, Pittsburgh, Pa.

[21] Appl. No.: 521,081

[22] Filed: May 8, 1990

[51] Int. Cl.$^5$ .............................................. A61B 5/00
[52] U.S. Cl. .................................. 128/634; 128/633; 250/364; 356/39; 422/55
[58] Field of Search .................. 128/631, 633, 634; 356/39, 418, 419; 250/364, 365; 422/55

[56] References Cited

U.S. PATENT DOCUMENTS

| | | | |
|---|---|---|---|
| 3,123,866 | 3/1964 | Stewart et al. | 19/197 |
| 3,461,856 | 8/1969 | Polanyi | 128/633 |
| 3,638,639 | 2/1972 | Merrill et al. | 128/768 |
| 3,785,772 | 1/1974 | Coggeshall | 128/632 |
| 3,787,119 | 1/1974 | Rybak | 128/633 |
| 3,939,350 | 2/1976 | Kronick et al. | 356/36 |
| 4,344,438 | 8/1982 | Schultz | 128/634 |
| 4,558,014 | 12/1985 | Hirschfeld et al. | 436/527 |
| 4,572,106 | 2/1986 | Mills | 119/14.47 |
| 4,577,109 | 3/1986 | Hirschfeld | 250/461.1 |
| 4,755,667 | 7/1988 | Marsoner et al. | 356/417 |
| 4,815,843 | 3/1989 | Tiefenthaler et al. | 356/136 |
| 4,849,172 | 7/1989 | Yafuso et al. | 436/136 |
| 4,857,273 | 8/1989 | Stewart | 436/805 |
| 4,861,727 | 8/1989 | Havenstein et al. | 436/136 |
| 4,877,747 | 10/1989 | Stewart | 356/432 |
| 4,892,383 | 1/1990 | Klainer et al. | 128/634 |
| 4,892,640 | 1/1990 | Wolfbeis et al. | 204/418 |
| 4,954,318 | 9/1990 | Yafuso et al. | 422/59 |
| 4,999,306 | 3/1991 | Yafuso et al. | 436/68 |

OTHER PUBLICATIONS

Wolfbeis, "Fiber-optic Sensors in Biomedical Sciences," Pure and Appl. Chemistry, vol. 59, No. 5, pp. 663-672 (1987).

Schultz, "Sensitivity and Dynamics of Bioreceptor-based Biosensors," Annals of the New York Academy of Sciences, vol. 506 (1987).

Thromberg et al., Anal. Chem., vol. 59, pp. 1226-1230 (1987).

Anderson and Miller, Clinical Chemistry 34/7, pp. 1417-1421 (1988).

Oi et al., J. Cell biol., vol. 93, p. 981 (1982).

Bhatia et al., SPIE vol. 1054, Fluorescence Detection III (1989).

Primary Examiner—David M. Shay
Attorney, Agent, or Firm—Arnold B. Silverman

[57] ABSTRACT

A device and method for measuring properties of certain substances such as analytes are provided. The device includes a probe housing having an optical fiber associated therewith. The housing is capped on one end by a porous membrane which is permeable to the analyte being studied. The housing also includes a reflective surface member disposed between the end of the optical fiber and the membrane, thereby defining a chamber. The reflective surface member does not allow light to be transmitted into or out of the chamber. However, a dye-labeled analog-analyte can permeate the reflective surface member and thereby allow a measurement to be taken which is related to the concentration of the analyte being studied. An embodiment for use in vivo is provided. A related method is also provided.

17 Claims, 3 Drawing Sheets

OPTICAL FIBER SENSORS FOR CONTINUOUS MONITORING OF BIOCHEMICALS AND RELATED METHOD

BACKGROUND OF THE INVENTION

1. Field of the Invention.

This invention relates to devices for measuring the concentration of certain biochemical constituents in samples. More particularly, the invention relates to a fiber optic device and related method which utilizes a reflective surface to enhance the emitted signal and to reduce the effects of excitation light when the sensor is operating.

2. Description of the Prior Art.

It has become increasingly important in analytical and clinical chemistry to have the capability of remote sensing of chemical and physical parameters. Some methods of performing this type of sensing have been known, such as potentiometry, amperometry, piezoelectric mass determination, conductivity and measurement of reaction enthalpy.

In addition to these methods, optical fibers can be used for remote sensing of analytes and other substances. Optical sensors have certain advantages over electrochemical sensors. For example, optical sensors do not require reference cells and optical sensors are immune to electromagnetic interferences. Further, the use of optical fibers can be advantageous when the samples are relatively inaccessible, for instance, in case of in vivo tests. Optical fiber waveguides allow the transportation of an optical signal over large distances from the sample to an associated meter, for example. Optical fibers can be exposed to varying environments without suffering substantial destruction or deterioration as a result. Optical fibers are also biocompatible which makes them desirable for use in invasive medical procedures. For a general discussion of sensors and of optical fiber sensors in particular see Wolfbeis, Fibre-optic Sensors in Biomedical Sciences, Pure and Appl. Chemistry, Vol. 59, No. 5 pp. 663-672 (1987).

It has been known to provide optical fiber sensors of various types. U.S. Pat. No. 4,334,438, the inventor of which is one of the co-inventors hereof, is hereby incorporated herein by reference. This patent U.S. Pat. No. 4,334,438 relates to a fiber optic sensor having a chamber containing a dialysis membrane which allows selected plasma constituents to pass therethrough and enter the chamber. The chamber contains specific receptor sites in the form of binding agents each of which reversibly binds with one of the plasma constituents. The chamber also contains competing ligands which are dye-labeled. They compete with the plasma constituents for the specific receptor sites on the binding agents. The competing ligands are chosen for their particular optical properties and molecular size so that they do not escape back out of the sensor into the bloodstream. The intensity of light emitted from or absorbed by the receptor-site/competing ligand complexes or the free competing ligand alone can be measured by a fluorimeter. This measurement gives a quantitative indication of the concentration of plasma constituents in the blood.

One limitation of this system is that the response time is on the order of minutes due to the time it takes for diffusion of the molecules being studied across the membrane and along the chamber. Further, as the fluorescently labeled compound is bound to the wall, the optical fiber must be inserted exactly straight inside the hollow fiber so that the amount of baseline fluorescence due to the dye-labeled competing ligand bound to the wall is minimized. Further, the skin of the membrane must remain immersed in a buffer solution. Otherwise, if it is exposed to air, the membrane begins to dry and diffusion of the analyte into the sensor is dramatically affected. Because of this, the assembly must be glued together while it is submerged in the buffer. The glue seams must form a tight seal because with any leak, the chemical constituents of the sensor can escape. The hollow fiber configuration can also exhibit lack of stability such that any movement of the sensor while in use affects the signal response. In addition, during assembly the proteins which are immobilized are pumped through the fiber with pressure. This flow method results in variations in the amount of immobilized material along the inside wall, due to variations in the spongy surface. There remains a need, therefore, for a sensor which overcomes those disadvantages.

It has also been known to provide other types of fiber optic sensors. For example, U.S. Pat. No. 4,892,383 discloses a fiber optic sensor which includes a modular reservoir cell body and a semi-permeable membrane, however, the sensor requires use of a reagent which precludes reversibility. See also U.S. Pat. No. 4,892,640 which discloses a sensor for determining electrolytic concentrations using an ion selective membrane.

U.S. Pat. No. 4,849,172 discloses an optical sensor having a gas permeable silicone matrix that contains a high concentration of an optical indicator consisting essentially of a mixture of derivatives of a polynuclear aromatic compound U.S. Pat. No. 4,853,273 discloses another type of sensor involving enhancement of a light signal response by incorporating a partially reflecting, partially transmitting medium between a coupling structure and an optically dense body.

Optical sensors based on generating a resonance signal in a metallic medium have also been known. See U.S. Pat. No. 4,877,747. Other sensors based on detection of refractive index charges in gaseous liquids, solids or porous samples have been known. See U.S. Pat. No. 4,815,843 and U.S. Pat. No. 4,755,667. Sensors for measuring salt concentrations have also been known. U.S. Pat. No. 4,572,106.

U.S. Pat. No. 4,577,106 discloses a remote multiposition information gathering system for obtaining thermometric information from remote locations using fiber optics.

U.S. Pat. No. 4,861,727 discloses a luminescent oxygen sensor using a lanthanide complex.

Other methods of measuring concentrations of biochemicals in blood include withdrawing blood from the patient and then analyzing it. For example, U.S. Pat. No. 3,785,772 discloses a device having a pair of syringes to withdraw blood from a patient, and a dialysis membrane to separate a particular blood constituent from the blood, a reactant which reacts with the chosen blood constituent to form a reactant—blood constituent complex the concentration of which is proportional to the concentration of the blood constituent. This system requires replacement of the reactant after each measurement because the reactant and the blood constituent form an irreversible complex. In addition, the system cannot give measurement of an instantaneous change in the concentration of the blood constituent because of the time taken to remove the blood from the body and obtain a reaction with the reactant.

U.S. Pat. No. 3,638,639 also shows measurement of blood constituents outside the body. In this system, a catheter is inserted into the blood and lipids are passed through a membrane in the catheter and are dissolved in a solvent which is sent out of the body to be analyzed.

U.S. Pat. No. 3,939,350 shows a system for carrying out immunoassays using fluorescense to indicate the presence of a ligand to be detected. An analog liquid is bound to a transparent sheet and contacted with an aqueous assay solution containing the ligand to be detected associated with fluorescent molecules. The ligands become bonded to the sheet and light is passed there through to cause fluorescence.

U.S. Pat. Nos. 3,123,866, 3,461,856 and 3,787,119, all disclose means to measure properties of the blood in vivo. These comprise optical catheters inserted into the blood for measuring the intensity of light reflected from the blood thereby indicating the blood's oxygen content. None of the aforementioned patents, however, are specifically designed for measuring the concentration of plasma constituents, such as glucose, in a continuous, reversible manner.

Despite these prior art methods and devices, there remains a need for an optical fiber sensor which has increased sensitivity and a shorter response time. Further there remains a need for a device where the active element is of shorter length and a sensor which is easier to assemble than conventional designs. There also remains a need for a sensor which provides greater excitation signals and simultaneously captures a greater percentage of the emitted light from a molecule to be analyzed by reflecting back into the fiber light which is emitted in directions opposite to the fiber location. There remains a further need for a device and method which may be used to measure either free dye-containing molecules or bound dye-containing molecules and which has the capability of providing continuous monitoring of the concentration of an analyte.

SUMMARY OF THE INVENTION

These and other needs are satisfied by the device and method of the present invention which provides an optical fiber sensor having a probe member used in conjunction with an optical fiber. As used herein, the term "fiber" shall include a single optical fiber as well as a bundle of optical fibers. In a preferred form, the probe member of the device of the present invention includes a first region into which excitation light may pass from the optical fiber. Adjacent to the first region is a second region which is protected from receiving light by a porous reflective surface member which communicates with the first region such that molecules may pass from the first region into the second region. In a preferred form the reflective surface resists penetration of excitation light into the second region. The second region is thus a dark region. The opposite end of the second region contains a membrane through which the analyte to be studied can diffuse. In addition, there are immobilized receptors bound within either the first region or the second region.

The sensor is placed in contact with the substance to be analyzed, referred to herein as the analyte. The analyte may be any soluble, macro-molecule which is mobile. It may be a water soluble molecule. The analyte passes through the membrane into the second region. In a preferred form, the immobilized receptors are contained in this second region. There, the analyte competes with a dye-labeled substance which is similar in chemical properties to the analyte. This dye-labeled substance will be referred to herein as the "analog-analyte." The analyte and the analog-analyte compete to bind with the immobilized receptors. The dye-containing analog-analyte molecules which do not combine with immobilized receptors then pass through the reflective surface member into the first region. Upon excitation, the fluorescent dye causes light to be emitted from the dye-containing analog-analyte molecules, and this light signal is then transmitted back along the fiber and is measured. The measurements are then used to determine the concentration of the particular analyte contained in the sample.

It is an object of the invention to provide a sensor with increased sensitivity to dye-containing analog-analytes, and which may be utilized for studying either bound or free dye-containing substances, in a continuous, reversible manner.

It is another object of the invention to provide a sensor which is of a smaller length but still provides increased sensitivity.

It is another object of the invention to provide a sensor which uses a flat membrane thus eliminating the need for hollow fiber membranes as well as reducing the number of glue seals required.

It is another object of the invention to provide a sensor which is easy to manufacture and easy to use and handle by inexperienced personnel.

It is another object of the invention to provide a sensor which provides durability and having membranes which may be easily changed or replaced without difficulty in alignment on insertion of the membrane.

It is a further object of the invention to provide a device which has a stable response for long periods of time.

It is yet a further object of the invention to provide a method of analyzing and measuring chemical substances which is reliable and easy to perform in a variety of settings.

These and other objects of the invention will be fully understood from the following description of the invention with reference to the drawings appended to this Application.

BRIEF DESCRIPTION OF THE DRAWINGS

FIG. 1A is a schematic cross-sectional illustration of one embodiment of the sensor of the present invention and shows a seal means dividing the chamber into separate liquid tight zones.

DESCRIPTION OF THE PREFERRED EMBODIMENTS

Figure 1:
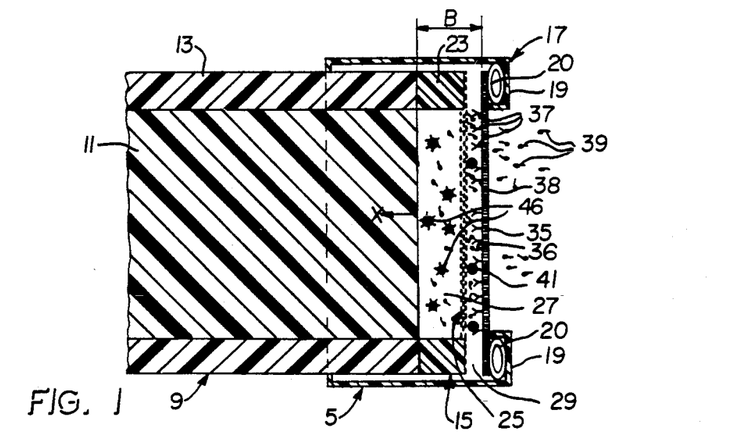
FIG. 1 is a schematic cross-sectional illustration of one embodiment of the sensor of the present invention.

Referring to FIG. 1, the sensor is composed of an optical fiber 9 which extends into a probe housing 5. Probe housing 5 is preferably cylindrical cap member composed of stainless steel, tetrafluoroethylene (known commercially as "Teflon") or polycarbonate, and most preferably is composed of polycarbonate. The dimensions of probe housing 5 vary depending on the application in which it is to be used, however, the overall length is typically about 5 to 100 mm and preferably about 10 to 20 mm.

In accordance with one aspect of the invention, optical fiber 9 which as defined hereinbefore may be a bundle of fibers or a single fiber, has probe housing 5 capped on one end thereof. Optical fiber 9 has core 11 and cladding 13. There may also be an outside protective coating placed on the optical fiber 9 (not shown).

Core 11 has a cross sectional diameter of about 0.1 to 3 mm and preferably about 0.5 to 1.5 mm. As discussed more fully hereinafter, the sensor of the present invention allows for use of a core having a greater diameter. The core diameter is related to sensitivity of the fiber in that up to a thickness of about 1 mm sensitivity to light increases with increase of the core diameter. Thus, it is an advantage to be able to accomodate fibers of a wide range of core diameters as is done in accordance with the present invention so that the sensitivity of the device can be optimized.

Probe housing 5 terminates at annular re-entrant flange 19 at sensor end 17. The cross-sectional shape of probe end 15 is preferably round but it may also be square, oval, circular, triangular or other shapes.

A porous reflective surface member 25 is placed within probe housing 5 adjacent to the end of optical fiber 9. Reflective surface member 25 is composed of a material which is porous to the analog-analyte discussed hereinafter, and which has at least one reflective side facing towards the optical fiber 9 which reflects light back towards optical fiber 9 while resisting travel of light through it towards end 17 of the sensor. Reflective surface member 25 acts as a porous mirror. It reflects light coming from optical fiber 9 back in the direction marked by the arrow X. It substantially resists light from passing through it towards end 17 of the sensor. In this way, reflective surface member 25 divides probe housing 15 into an illuminated region 27 and a dark region 29. Illuminated region 27 is bounded by a spacer 23 on the one hand and reflective surface member 25 on the other hand. Dark region 29 is bounded by reflective surface member 25 and ultrafiltration dialysis membrane 35, which is discussed more fully hereinbelow.

Reflective surface member 25 may be composed of a noble metal such as silver, gold or platinum alloy or other reflective surface. The reflective surface member 25 may be created by depositing the metallic substance using sputtering techniques on to a porous membrane. Alternatively, two sheaths of metal with offset openings could be used which would allow molecules to pass therethrough but would not allow the passage of light therethrough.

It should have a porosity of about 0.1 micron to 3.5 microns so as to allow molecules such as bovine serum albumin, dextran or Immunoglubulin G or other proteins to pass therethrough. Reflective surface member 25 may have a diameter of about 0.6 to 3.5 mm so that it is at least of equal size to cover core 11 of optical fiber 9 substantially completely. The thickness of reflective surface member 25 is preferably about 1 micron to 100 microns.

Probe housing 5 is substantially closed at end 17 by a membrane 35. Membrane 35 is semi-premeable and is preferably an ultra fitration "UF" dialysis membrane which may be composed of cellulose acetate, cellulose or polysufone and preferably it is composed of cellulose acetate. It should be noted, however that many other types of materials are available for use as semi-permeable membranes such as membranes containing mobile carriers or bi-layer membranes containing selective pores. Membrane 35 should have a porosity of about 5,000 MWCO to 25,000 MWCO where "MWCO" means molecular weight cut off as would be understood by those skilled in the art. The analyte to be tested must be able to pass through it into dark region 29. The thickness of membrane 35 is preferably about 0.005 to 0.1 mm. In accordance with one aspect of the invention membrane 35 is pressed directly onto reflective surface member 25. In FIG. 1, the two elements are shown as separate for convenience of disclosure. It is noted that although they are pressed together, molecules may still move between the two within the chamber. Membrane 35 is held in place, preferably by O-ring or compression type seals 20 which are compressed when housing 5 is placed over membrane 35. It is noted that this reduces the need for any glue seams which can harm the proteins which may be contained in the analyte or other substances, and as discussed hereinbefore, glue seams can affect durability of the sensor.

Membrane 35 has bound to its inner wall 36 an immobilized receptor which may consist of antibody, enzyme, other bioreceptors, or receptor proteins. This creates receptor sites 37 as shown in FIG. 1. The immobilized receptor is a binding agent, each molecule of which can reversibly bind with one or more of the analyte constituent molecules, as discussed more fully hereinafter. The analyte being tested is designated by reference character 39 in FIG. 1.

The receptor sites 37 are created when the immobilized receptor material is coated onto inner wall 36 of membrane 35 prior to assembly of the sensor. The immobilized receptor is coated onto membrane 35 to a thickness of about 30 angstroms to several microns to create sufficient receptor sites to allow accuracy in measurements as discussed hereinafter.

Probe housing 5 also contains an "analog-analyte" designated by reference character 41. As used hereinafter, the term "analog-analyte" includes a competing substance which has properties similar to the analyte. The analyte may be any mobile macromolecule including any water-soluble biochemical. The analog-analyte competes with the analyte for the opportunity to bind with an immobilized receptor at an immobilized receptor site 37. As it has properties similar to the analyte 39 used in the particular application, it is called an analog-analyte. The analog-analyte 41 is chosen for its particular optical properties and molecular size, so that it will adequately compete with analyte 39 for receptor sites 37. If an analog-analyte for a particular analyte does not exist, one can be created by binding a large protein such as bovine serum albumin with the analyte in a manner which would be understood by those skilled in the art.

The reaction which takes place can be summarized by the following equations:

(1)

(2)

In accordance with Equation 1, the analog-analyte binds with a receptor to form an analog-analyte-receptor complex. When the analyte is introduced into the system, it may then bind with that receptor to form an analyte-receptor complex as stated in Equation 2. This frees the previously bound analog-analyte.

Referring to FIG. 1, the analog-analyte 41 is bound to a receptor 37. This forms the Analog-Analyte-Receptor Complex set forth in Equation 1 above. As analyte molecules 39 diffuse through membrane 35, they bind with receptors at receptor sites 37 an example of which is designated by reference character 38. This frees the analog-analyte molecules which had been bound at those receptor sites. The free analog-analyte molecules then pass through porous reflective surface member 25 into illuminated region 27. There, the analog-analyte molecules fluoresce in response to excitation energy sent through optical fiber 9 and they are designated in their fluorescent state by reference character 46. For a general discussion of bioreceptors as used within sensors, see Schultz, *Sensitivity and Dynamics of Bioreceptor based Biosensors*, Annals of the New York Academy of Sciences, Vol. 506 (1987)

In order to cause fluorescence, and thereby allow detection by optical fiber 9, the analog-analyte 41 should be fluorescently labeled by covalent coupling with an appropriate dye as is known to those skilled in the art. A suitable dye-containing analog-analyte is Flourescein Isothiocyanate-dextran known as FITC-dextran. Other dye containing analog-analytes are FITC anti-rabbit IgG as disclosed by Tromberg et al., Anal. Chem. Vol. 59 pp. 1226–1230 (1987); Texas red as disclosed by Anderson and Miller, Clinical Chem. 34/7, pp. 1417–1421 (1988); and phycobiliprotein disclosed by Oi et. al, J. Cell Biol. Vol. 93, p. 981 (1982).

Although specific examples have been cited, the principle of the present invention applies equally to any analyte-receptor system whose equilibrium binding constant permits free exchange with the analog-analyte.

As mentioned hereinbefore, when the sensor is exposed to analyte 39 in solution, the analyte 39 penetrates membrane 35, and enters dark region 29 of the sensor. A competitive reaction takes place between analyte 39 and analog-analyte 41 for receptor sites 37.

The optical fiber 9 in this configuration shines the excitation light parallel to the oncoming analyte 39. As a result, a means of blocking its "view" of the dye saturated analog-analyte is desirable. This is provided by reflective surface member 25, discussed hereinbefore, which is preferably disposed between the immobilized receptor sites 37 and the optical fiber 9. When the sensor is not in contact with an analyte 39, the analog-analyte 41 is bound to the immobilized receptor in sites 37 and the reflective surface member 25 will prevent the return of most of the emission light coming through fiber 9. When the sensor is placed in a solution of analyte 39, the analog-analyte 41 will be free to diffuse through reflective surface member 25 into the illuminated region 27 in view of optical fiber 9.

The distance between the optical fiber 9 and the UF membrane 35 should be about 25 to 100 microns and is preferably about 50 microns. This distance is shown in FIG. 1 by the reference character B. The determination of this distance is based on the following factors: A very short distance B can lead to lower sensitivity. At about 25 microns, the signal is about twenty-five percent of the signal achieved by a bare optical fiber in a solution of equivalent fluorphore whereas at about 100 microns, the signal is at about 80 percent, depending upon the concentrations of fluorophore. However, longer distances result in a longer response time because of the requirement of analyte diffusion and consequent analog-analyte diffusion. Therefore, the reflective surface member 25 should not be too close to the end of the fiber so that signal strength is lost, but it should not be at a long distance such that response time is affected. As noted, the preferred distances between the membrane 35 and the end of the fiber 9 for this embodiment of the present invention are between about 25 to 100 microns and preferably about 50 microns.

For simplicity of disclosure, a system has been described which uses a single analyte and a single analog-analyte. However, with minor adaptions the system can as easily be used with multiple analytes and corresponding analog-analytes. For example, as show in FIG. 1A, the reflective surface member 25 and the membrane 35 may be sealed off into various zones 47 in a checkerboard configuration. In such a case each zone 47 represents different concentrations of a single analyte and the device so constructed can be used for calibration purposes. Alternatively, the various zones 47 may be sealed off from one another and each zone 47 may contain a different analyte and analog-analyte combination. Multiple optical fibers would be used to read the information from the various zones 47. Alternatively, the information may be read by a suitable optical scanning device as would be understood by those skilled in the art.

Figure 2:
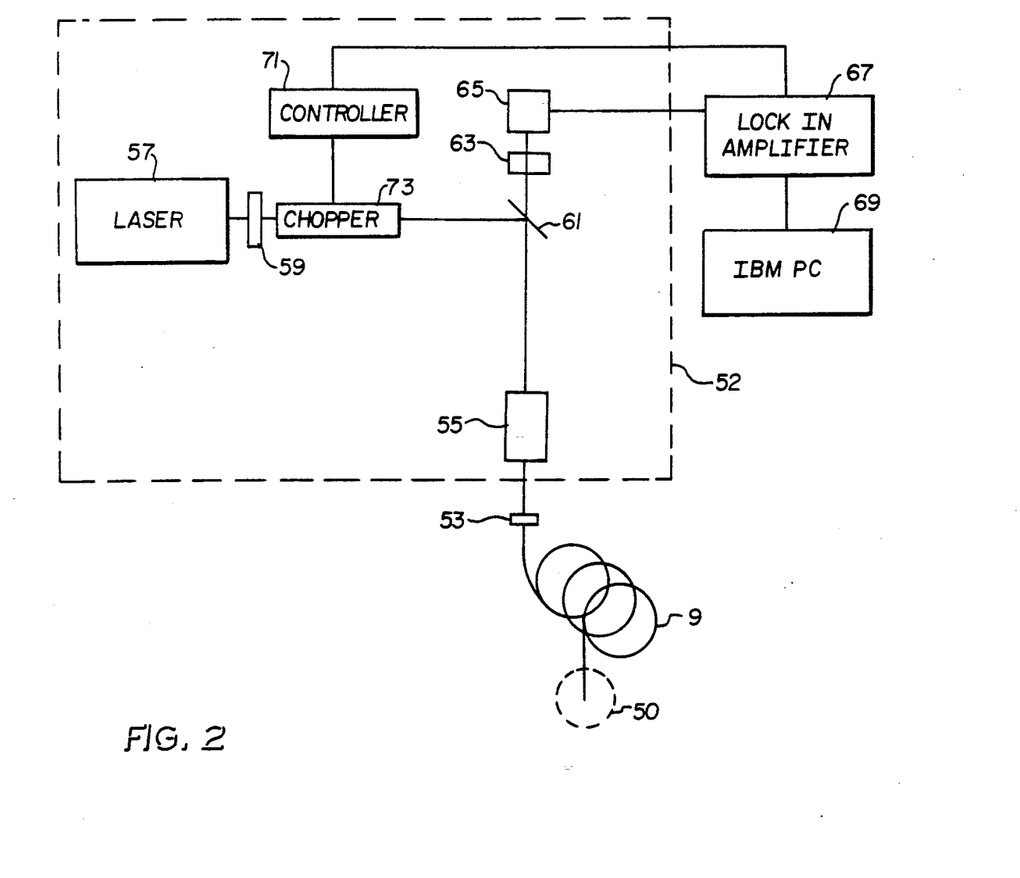
FIG. 2 is a combined schematic illustration and block diagram of a system which may employ the device and method of the present invention.

Referring now to FIG. 2, one embodiment of the present invention is shown in conjunction with a system for reading signals obtained from the sensor of the present invention.

Optical fiber 9 has a probe housing (not shown) attached to one end thereof which is placed in a sample 50 to be tested. The sample could be either in vivo or it may be in vitro. Optical fiber 9 is connected by connector 53 to a fluorimeter 52 having the components discussed hereinafter. Fluorimeters may be obtained commercially in a single kit. For example, such a fluorimeter is commercially available from ORD Corporation. In addition, a fluorimeter having a laser as the light source has been described by S. K. Bhatia, et. al, SPIE Vol. 1054, Florescence Detection III (1989).

The fluorimeter is composed of the components of FIG. 2 contained in dashed box 52. Excitation light is generated by light source 57. Energy is transmitted by light source 57, which may be a helium laser, through filter 59. Chopper 73 acts to chop the light at a predetermined frequency and this is done in conjunction with lock-in amplifier 67. Lock-in amplifier 67 substantially reduces all background signal which is not being modulated at that predetermined frequency. For example, interference in line voltages or ambient light interferences are substantially removed. The lock-in amplifier 67, which is now available as part of a fluorimeter package such as that mentioned hereinabove, has a very high signal-to-noise ratio.

Controller 71 can be used to control the frequency at which chopper 73 operates in a manner which will be understood by those skilled in the art. The frequency may be any amount which is out of phase with the line voltage, that is, it must be other than 60 cycles or 120 cycles.

The excitation wavelength of the light generated by source 57, on the other hand depends upon the dye being used. A typical range would be between about 450 to 850 nanometers for excitation and emission signals.

Dichroic beam splitter 61 is placed in the path of laser energy emitted from light source 57. Beam splitter 61 serves to bend the excitation wavelength about 90 degrees in the configuration shown in FIG. 2, however, beam splitter 61 can be positioned appropriately to divide excitation light from emission light as desired in the particular application.

On emission of light through optical fiber 9, emission light passes through optical coupler 55, through beam splitter 61 to dye filter 63. Dye filter 63 acts to filter out any excitation light that may be reflecting back from the optical fiber 9. There could be interference of the emission signal by the excitation light. For this reason, a dye with a greater Stoke's shift is preferred as would be understood by those skilled in the art.

The fluorescent light signal which is passed through filter 63 is sensed by a detector 65. The detector may be a photodiode or it may be a photomultiplier tube.

Detector 65 converts the light signal sensed from optical fiber 9 of the sensor into a corresponding voltage signal which is then amplified by lock-in amplifier 67. In addition, lock-in amplifier 67 serves to reduce the effects of noise in the signal.

This information can be analyzed by a microcomputer 69 such as an IBM-PC which is programmed in a suitable manner as would be readily understood by those skilled in the art. The analysis involves measuring a signal corresponding to the amount of free fluorescent analog-analyte 46 which diffuses into illuminated region 27 (FIG. 1). When this free analog-analyte 46 fluoresces the light signal is emitted. The amount of analog-analyte 46 is proportional to the concentration of analyte 39 in the sample. In this way the concentration of analyte present can be accurately determined.

It should be understood that although FIGS. 1 and 2 relate to measurement of free analog-analyte, the present invention also embraces use of the sensor to measure the bound analog-analyte. In that case, the dye-labeled analog-analyte would bind with receptors coated onto the wall of the reflective surface member 25 which is in the illuminated region 27. It may be desirable in certain instances to provide a signal of such bound analog-analyte and this is provided for within the present invention.

It is also noted that the immobilized receptors may be coated on the wall of reflective surface member 25 which faces into the dark region 29 instead of having the receptors 37 on the wall of membrane 35. This may be desirable for ease of manufacture, or in certain instances depending upon the receptors or the dye used in a particular instance.

Figure 3:
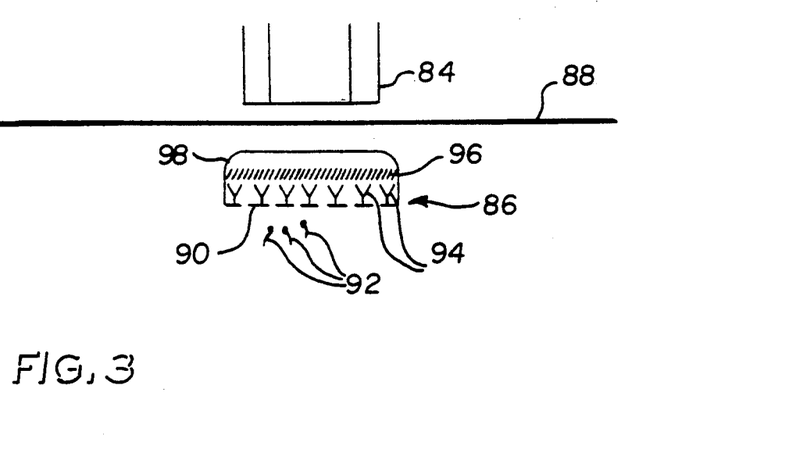
FIG. 3 is a schematic cross-sectional illustration of another embodiment of the invention which is suitable for use in vivo.

In accordance with another aspect of the invention the probe housing which contains the membrane and the reflective surface member may be a unit separate from the optical fiber. Referring to FIG. 3, optical fiber 84 is separate from the sensor unit 86. The sensor unit 86 may be utilized in vivo and, as shown in FIG. 3, it may be placed under the skin 88 of a patient. Alternatively, in certain applications, the sensor unit 86 can be placed directly on the skin (not shown) in which case the analyte would diffuse through the skin and into the unit 86.

The penetration of analyte from tissue through the skin can be accelerated by appropriate creams or medications which are available.

Sensor unit 86 is composed of semi-permeable membrane 90 which as stated hereinbefore with respect to the embodiment shown in FIG. 1 is permeable by analyte 92. The unit 86 includes immobilized receptors 94. The unit 86 may have immobilized receptors 94 coated on to membrane 90 as shown in FIG. 3. Alternatively, the receptors 94 could be coated on one wall of reflective surface member 96. Preferably, immobilized receptors 94 are coated onto the internal wall 99 of porous membrane 90 as shown in FIG. 3. The unit 86 could then be covered by transparent film 98. Sensor unit 86 also contains an analog-analyte (not shown) appropriate for the analyte being tested in the particular application. The unit 86 would be submerged in the analyte and the competitive reaction between the analog-analyte and the analyte would take place as discussed hereinbefore in detail with reference to FIG. 1.

It will be appreciated that in accordance with the embodiment shown in FIG. 3, the entire sensor unit 86 could be implanted under the skin. As the skin is capable of being penetrated by light, a light source would be used to shine excitation light onto the area of the skin 88 above the sensor unit 86 and a detector could then be used to measure the emission signal. Sensitivity to the signal may be somewhat reduced with this embodiment, however it is not reduced to a large degree as the sensitivity of available fiberoptic fluorimeters is typically greater than about $10^{-12}$ M which would provide sufficient strength to obtain an accurate signal.

Figure 4:
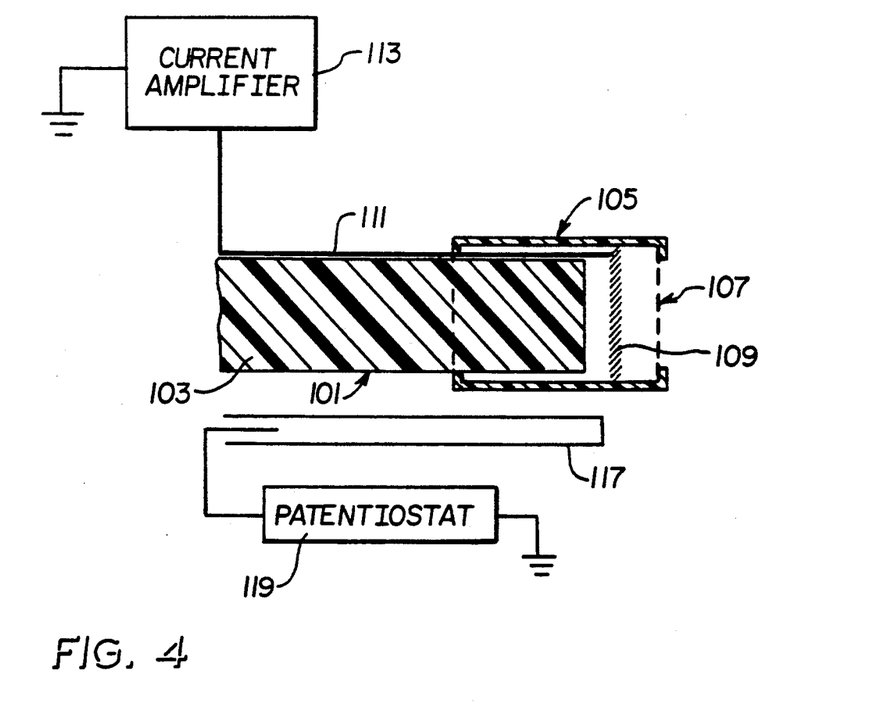
FIG. 4 is a schematic illustration and block diagram of one embodiment of the invention in which the reflective surface member is held at a predetermined electrical potential.

Another embodiment of the invention is shown in FIG. 4. A sensor 101 is constructed in a manner similar to that discussed with reference to FIG. 1. Optical fiber 103 is placed within probe housing 105. Probe housing 105 has at one end thereof a porous dialysis membrane 107. Also contained within probe housing 105 is a porous reflective surface member 109 similar to that discussed hereinbefore.

In the embodiment of FIG. 4, however, the conductive potential of reflective surface member 109 is utilized. The reflective surface member 109 is placed at either a negative potential or a positive potential depending upon the particular application and is attached by connector 111 to a current amplifier 113 which is used to amplify the flow of charge at member 109. The solution being measured (not shown) contains charged ions in accordance with this aspect of the invention. The reflective surface membrane 109 being at a potential will affect the ionic concentrations of the environment around it and, hence, the pH of the solution. Changing the pH of the solution will generally affect the binding of the receptor proteins. In certain instances, it is desirable to increase the dissociation constant which, as would be understood by those skilled in the art, can be a result of an increase or a decrease in pH. This is used to facilitate a reaction where a change in pH is required or desirable for the competitive reaction to take place.

As shown in FIG. 4, a reference electrode 117 is provided to create the potential difference between it and reflective surface member 109. A flow of charge occurs between electrode 117 and the working electrode which is actually the reflective surface member 109. As long as both the reference electrode 117 and working electrode 109 are submerged in the analyte solution (not shown), charge will flow between the two electrodes and this will affect the pH as stated hereinbefore. The potential of reflective surface member 109 is controlled by potentiostat 119.

Although not shown in FIG. 4, it should be evident that reference electrode 117 may alternatively be contained within probe housing 105 to form a compact unit.

Referring now to FIGS. 1 and 2, the operation of the sensor of the present invention will be discussed. When the sensor (FIG. 1) is exposed to analyte 39 in solution, analyte 39 passes through membrane 35 into dark region 29. Dark region 29 contains dye-labeled analog-analyte 41. A competitive reaction takes place between the analyte 39 and analog-analyte 41 for receptor sites 37, which are secured to internal wall 36 of membrane 35. The analog-analyte 41 is chosen such that the association rate constant is similar to that of the analyte 39. The free analog-analyte 41 which does not bind with a receptor, diffuses across reflective membrane 25 into illuminated region 27.

The fluorescent dye in the analog-analyte 41 emits fluorescent light in response to excitation energy generated by light source 57. The fluorescent light signal emitted by the free analog-analyte 41 is filtered by dye filter 63 and thereafter the signal is sensed by detector 65. The voltage signal from detector 65 is amplified, noise is filtered out, and the signal is processed by microprocessor 69. The increase in fluorescence measured by the detector 65 is directly related to the concentration of the analyte 39 in solution.

Figure 5:
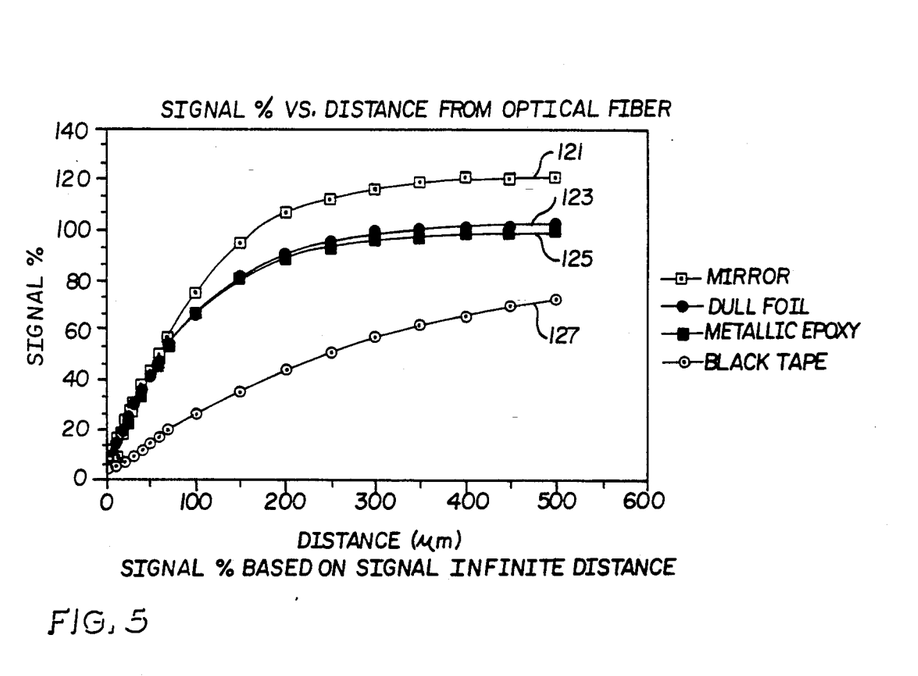
FIG. 5 is a graph showing a comparison of optical signals from a fluorescent solution with a mirror, a dull foil, metallic epoxy and black tape placed at various distances from the end of an optical fiber.

The operation of the reflective surface member of the present invention can be further understood with reference to FIG. 5.

FIG. 5 is a graph showing a comparison of fluorescent signals through a detector as a function of distance from the end of the optic fiber to the four surfaces described. The plot is of distance in microns along the abscissa and percent signal based on a signal at infinite distance (defined in the experiment of greater than 10 mm) along the ordinate. Curve 121 was generated using a photomultiplier-sensed fluorescent signal from an optic fiber having a mirror associated therewith. Curve 123 was generated using a detector which received fluorescent signals from an optic fiber which had dull foil surface associated therewith. Curve 125 was generated using a detector which received fluorescent signals from an optic fiber which had a metallic epoxy surface at the end of the fiber. And finally, curve 127 was generated using a detector which received fluorescent signals from an optic fiber which had black tape across it to prevent any reflection of the excitation or emission light. In each of the four experiments, the distal end of the optical fiber was placed in a solution of dye, in contact with the particular surface. The signal, generated by the photomultiplier tube, was read from the lock-in amplifer. Using a translation stage as would be understood by those skilled in the art, the surface was moved away from the optical fiber, and the new signal was read. This was repeated until the fiber was about 10 millimeters from the surface, at which time further distance did not result in increased signal. This final signal was used as the "signal at infinite distances." As is evident from FIG. 5, at distances less than about 70 microns, the mirror, dull foil and metallic epoxy, associated with curves 121, 123, and 125, respectively yield similar enhancements due to the added signal from the reflected light from these surfaces, over the black tape associated with curve 127. This shows that the optical quality of the reflective surface used in the sensor is not of great import in generating an enhanced signal, which results in ease of manufacture. It appears from these experiments as to optical properties, that having the reflective surface member 25 of the present invention close to the end of the fiber can provide a three fold increase in sensitivity of the sensor of the present invention.

Figure 6:
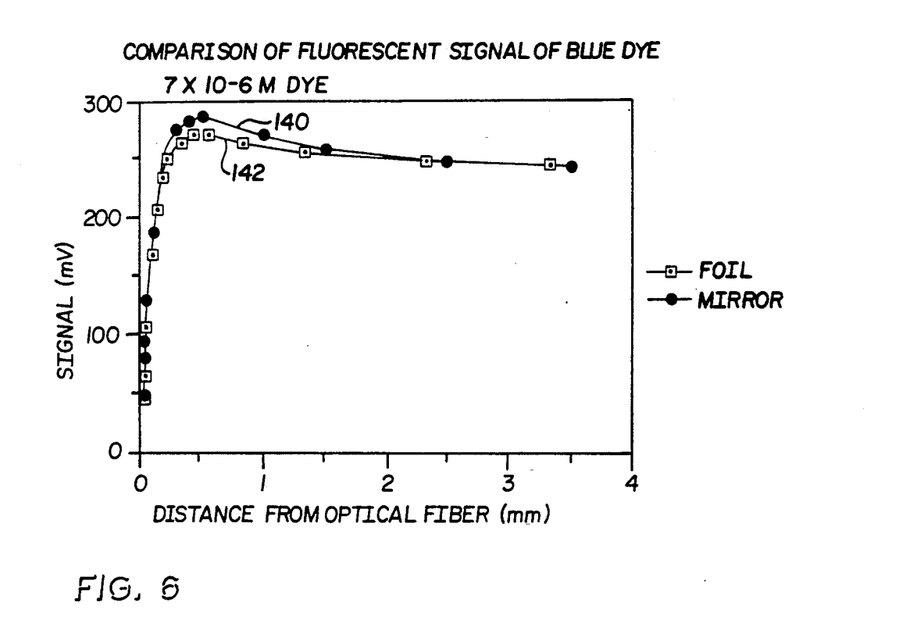
FIG. 6 is graph showing relative signal output as a function of optical distance.

Further details about the operation of the device of the present invention can be understood with reference to FIG. 6. FIG. 6 is a graph of distance of the optical fiber end in the fluorescent media to the reflective surface along the abscissa against signal strength in millivolts along the ordinate. Curve 140 shows a fluorescent signal generated using $7 \times 10^{-6}$ M blue dye from an optic fiber using a mirror. Curve 142 shows a fluorescent signal for an optic fiber using a foil membrane surface. FIG. 6 is similar to FIG. 5, however, it should be noted that the distance covered by curves 140 and 142 is much longer than shown in FIG. 5. It is noted that there is a greater sensitivity obtained over the shorter distances of about 1 to 600 microns of FIG. 5 whereas FIG. 6 shows the initial difference in sensitivity which then levels off at over the longer distances of about 2.5 to 3.5 mm. Both Figures show that an enhancement of the signal can be achieved independently of the optical quality of the mirror. This shows that the present invention may be manufactured using very small sizes of reflective surfaces and a variety of types of reflective surfaces, thus allowing for ease of manufacture, lower cost and more versatile applications.

Referring now to the method of the present invention, a sample is taken which includes an analyte 39 to be studied. A sensor (FIG. 1) is immersed into a sample. Readings may be taken periodically as the device is primarily to be used for continuous monitoring of the concentration of the analyte in the sample. The analyte 39 is permitted to diffuse across membrane 35 (FIG. 1) into dark region 29. A competitive reaction is allowed to proceed. During this reaction, the analog-analyte 41 which contains a fluorescent dye competes with analyte 39 to bind with an immobilized receptor at a receptor site 37. As the reaction occurs molecules of analoganalyte which remain unbound are permitted to diffuse across reflective surface member 25 into light region 27. The distance between membrane 35 and reflective surface member 25 is sufficiently small such that the response time of the sensor is at least less than about one minute.

A fluorescent signal is emitted in all directions from the fluorescent molecule. Some fluorescent light is transmitted in direction X into optical fiber 9, but some of the signal is also emitted in the opposite direction. This signal emitted in the opposite direction is bent 180° by reflective surface member 25 so that it, too, will travel in the direction X and be transmitted by optical fiber 9. The signal sensed by optical fiber 9 is filtered to remove excitation light and it is then converted to a voltage signal by detector 65. Thereafter, the voltage signal is processed and the information is used as appropriate in the particular application.

It will be appreciated from the foregoing that the device and method of the present invention provides a sensor technique utilizing optical fibers which can be used for sensing of biochemicals, either in vivo or in vitro. It has increased sensitivity due to the fact that a greater portion of the emission signal is captured by the optical fiber. In addition, the excitation signal is enhanced by the reflective surface as well. The reflective surface member also allows for separation of the probe unit from the optical fiber which greatly increases the in vivo applications with which the device and method can be used. In addition, the larger diameter of the optical fiber allows greater sensitivity of the device. Further, the shorter lengths allow for easier manufacture and lower cost of manufacture.

Although the present invention has been described herein primarily in the context of bio-medical applications, it should be understood that the invention may also be used in a variety of other applications such as in environmental testing of, for example, PCB content in oils, and in other industrial applications.

Whereas particular embodiments of the invention have been described hereinabove for purposes of illustration, it will be evident to those skilled in the art that numerous variations of the details may be made without departing from the invention as defined in the appended claims.

What is claimed is:

1. A sensor for sensing properties of sample analyte, for use with light source means and detection means operatively associated with an optical fiber, comprising:
   a porous membrane, permeable to said analyte,
   porous reflective surface means adjacent to said porous membrane, for defining a chamber therebetween,
   dye-labeled analog-analyte in solution contained in said chamber,
   receptor material disposed within said chamber, and said receptor material being capable of chemically binding with said analyte and said analog-analyte, and
   transparent retention means wrapped across a wall of said reflective surface means facing out of said chamber such that said transparent retention means traps free dye-labeled analog-analyte which passes through said reflective surface means, and said retention means is transparent to an emission signal generated by fluorescence of said dye-labeled analog-analyte when said dye-labeled analog-analyte is excited with light.

2. A sensor for optically measuring properties of at least one sample analyte, comprising
   a probe housing,
   optical fiber means for transmitting light energy into and out of said housing, one end of said optical fiber means disposed within a hollow portion of said housing and spaced from one end of said probe housing,
   porous membrane means disposed generally adjacent said one end of said housing, for defining a chamber between an inner wall of said porous membrane means and said optical fiber means,
   reflective surface means disposed within said chamber between said optical fiber means and said porous membrane means, and spaced from said porous membrane means, said reflective surface means for defining an illuminated region between said one end of said optical fiber means and said reflective surface means and a dark region between said reflective surface means and said porous membrane means,
   a dye-labeled analog-analyte in solution disposed within said chamber,
   receptor material disposed within either said illuminated region or said dark region, and said receptor material being capable of chemically binding with said analyte and said analog-analyte,
   light source means for generating excitation energy, said light source means operatively associated with said optical fiber means such that said excitation light passes through said optical fiber means to said reflective surface means, and
   detection means operatively associated with said optical fiber means, for detecting an emission signal generated by said dye-labeled analog-analyte.

3. The sensor of claim 2 wherein said receptor material binds with
   said analyte which is water soluble biochemical.

4. The sensor of claim 2 wherein
   said receptor material is a substance selected from the group consisting of bioreceptors, enzymes, antibodies and receptor proteins.

5. The sensor of claim 2 wherein said porous membrane means is composed of a material selected from the group consisting of semi-permeable membranes, mobile carrier membranes, and bi-layer membranes.

6. The sensor of claim 2 wherein
   said reflective surface means is at least partially composed of noble metal material selected from the group consisting of silver, gold and platinum.

7. The sensor of claim 2 wherein said chamber has seal means for dividing said chamber into separate liquid-tight zones and said reflective surface means has corresponding sections each said section associated with one of said liquid-tight zones.

8. The sensor of claim 7 wherein said liquid-tight zones each contain a different analog-analyte corresponding to separate analytes and said detection means has means for reading a separate emission signal corresponding to each separate analyte.

9. The sensor of claim 7 wherein said liquid-tight zones each correspondence to a different concentration of said analyte.

10. The sensor of claim 2 wherein
    said reflective surface means has a porosity such that said analog-analyte may pass therethrough and be detected by said detection means by fluorescent light emitted from said analog-analyte and transmitted as an emission signal through said optical fiber means.

11. The sensor of claim 10 wherein
    said porous membrane means has a porosity such that said analyte may diffuse therethrough into said chamber and said porosity being such that diffusion of said dye-labeled analog-analyte out of said chamber is resisted.

12. The sensor of claim 10 wherein said receptor material is deposited onto said inner wall of said porous membrane means.

13. The sensor of claim 10 wherein said receptor material is deposited onto a wall of said reflective surface means which faces into said dark region.

14. The sensor of claim 10 wherein said receptor material is deposited onto a wall of said reflective surface means which faces into said illuminated region.

15. The sensor of claim 10, further comprising means for applying an electrical potential to said reflective surface means.

16. The sensor of claim 10 wherein said analog-analyte comprises a substance bound to the analyte.

17. The sensor of claim 16 wherein said substance is selected from the group consisting of bovine serum albumin, dextran and Immunoglobulin G.

* * * * *

UNITED STATES PATENT AND TRADEMARK OFFICE
CERTIFICATE OF CORRECTION

PATENT NO. : 5,143,066
DATED : September 1, 1992
INVENTOR(S) : CLAIRE KOMIVES and JEROME S. SCHULTZ It is certified that error appears in the above-identified patent and that said Letters Patent is hereby corrected as shown below:

Column 2, line 33, --.-- should be inserted after "compound".

Column 6, line 5, "semi-premeable" should be --semi-permeable--.

Column 7, line 27, --.-- should be inserted after "(1987)".

Column 8, line 21, "show" should be --shown--.

Claim 1, column 13, line 21, --a-- should be inserted after "of".

Claim 3, column 14, line 13, --a-- should be inserted after "is".

Signed and Sealed this

Ninth Day of August, 1994

Attest:

BRUCE LEHMAN

*Attesting Officer*     *Commissioner of Patents and Trademarks*